US012672859B2

(12) United States Patent
Guo et al.

(10) Patent No.: US 12,672,859 B2
(45) Date of Patent: Jul. 7, 2026

(54) METHOD AND CONTROL DEVICE FOR ADJUSTING OPENING SIZE OF SAMPLING WINDOW OF BIOPSY SURGICAL DEVICE

(71) Applicant: CHONGQING XISHAN SCIENCE & TECHNOLOGY CO., LTD., Chongqing (CN)

(72) Inventors: Yijun Guo, Chongqing (CN); Mingxuan Li, Chongqing (CN); Chaowei Li, Chongqing (CN); Li Cai, Chongqing (CN)

(73) Assignee: CHONGQING XISHAN SCIENCE & TECHNOLOGY CO., LTD., Chongqing (CN)

( * ) Notice: Subject to any disclaimer, the term of this patent is extended or adjusted under 35 U.S.C. 154(b) by 344 days.

(21) Appl. No.: 18/292,111

(22) PCT Filed: May 26, 2022

(86) PCT No.: PCT/CN2022/095130
§ 371 (c)(1),
(2) Date: Jan. 25, 2024

(87) PCT Pub. No.: WO2023/087657
PCT Pub. Date: May 25, 2023

(65) Prior Publication Data
US 2024/0341737 A1     Oct. 17, 2024

(30) Foreign Application Priority Data
Nov. 16, 2021    (CN) .......................... 202111355495.6

(51) Int. Cl.
A61B 10/02 (2006.01)
(52) U.S. Cl.
CPC ................................ A61B 10/0266 (2013.01)

(58) Field of Classification Search
CPC ............ A61B 10/0266; A61B 10/0275; A61B 2010/0208; A61B 2010/0225
See application file for complete search history.

(56) References Cited

U.S. PATENT DOCUMENTS

| | | | |
|---|---|---|---|
| 4,461,305 | A | 7/1984 | Cibley |
| 6,120,462 | A | 9/2000 | Hibner et al. |
| | | (Continued) | |

FOREIGN PATENT DOCUMENTS

| | | |
|---|---|---|
| CN | 101669809 A | 3/2010 |
| CN | 203688274 U | 7/2014 |
| | (Continued) | |

OTHER PUBLICATIONS

Decision of Grant for Chinese Application No. 202111355495.6 mailed Oct. 21, 2022.

(Continued)

*Primary Examiner* — Scott Luan
(74) *Attorney, Agent, or Firm* — Ballard Spahr LLP

(57) ABSTRACT

Disclosed are a method and control device for adjusting an opening size of a sampling window of a biopsy surgical device. The biopsy surgical device includes a motor, an outer cutter tube and an inner cutter tube. The outer cutter tube includes a sampling window on a side of the front end. The motor drives the inner cutter tube to move axially through a transmission mechanism, changing the axial relative position of the inner cutter tube and the sampling window. The method includes: obtaining an input instruction that includes a set value of an sampling window opening length; determining an axial movement distance of the inner cutter tube according to the current position of the inner cutter tube and the set value; calculating the number of rotations of the (Continued)

Obtaining an input instruction at least including a set value of an opening length of the sampling window

↓

Determining an axial movement distance of the inner cutter tube according to the opening length of the sampling window

↓

Calculating the number of rotations of the motor corresponding to the axial movement distance of the inner cutter tube

↓

Controlling the motor to rotate and detecting the number of rotations of the motor

↓

Controlling the motor to stop after the motor rotates for the corresponding number of rotations motor corresponding to the axial movement distance; and controlling the motor to rotate until the sampling window reaches the opening length.

20 Claims, 6 Drawing Sheets

(56) References Cited

U.S. PATENT DOCUMENTS

| | | | |
|---|---|---|---|
| 6,436,054 | B1 | 8/2002 | Viola et al. |
| 9,078,640 | B1 | 7/2015 | An |
| 2002/0077648 | A1 | 6/2002 | Lee et al. |
| 2006/0167475 | A1 | 7/2006 | Bischof et al. |
| 2013/0046316 | A1 | 2/2013 | Sullivan et al. |
| 2013/0096459 | A1 | 4/2013 | Vetter |
| 2015/0057569 | A1 | 2/2015 | Vetter et al. |
| 2016/0228105 | A1 | 8/2016 | Speeg et al. |
| 2018/0333146 | A1 | 11/2018 | Hallisey et al. |
| 2019/0059983 | A1 | 2/2019 | Germain et al. |
| 2019/0365361 | A1 | 12/2019 | Van Liere |
| 2020/0015794 | A1 | 1/2020 | Guo et al. |
| 2020/0187921 | A1 | 6/2020 | Ørts et al. |
| 2021/0038202 | A1 | 2/2021 | Klein et al. |
| 2021/0059748 | A1 | 3/2021 | Hsu et al. |

FOREIGN PATENT DOCUMENTS

| | | | |
|---|---|---|---|
| CN | 104188693 | A | 12/2014 |
| CN | 105796135 | A | 7/2016 |
| CN | 106388875 | A | 2/2017 |
| CN | 206745383 | U | 12/2017 |
| CN | 206745423 | U | 12/2017 |
| CN | 207084843 | U | 3/2018 |
| CN | 109199464 | A | 1/2019 |
| CN | 209529190 | U | 10/2019 |
| CN | 110420038 | A | 11/2019 |
| CN | 210644068 | U | 6/2020 |
| CN | 111700650 | A | 9/2020 |
| CN | 211534548 | U | 9/2020 |
| CN | 112510591 | A | 3/2021 |
| CN | 112587098 | A | 4/2021 |
| CN | 113017709 | A | 6/2021 |
| CN | 213606537 | U | 7/2021 |
| CN | 113243941 | A | 8/2021 |
| CN | 214157384 | U | 9/2021 |
| CN | 113476111 | A | 10/2021 |
| CN | 114027888 | A | 2/2022 |
| CN | 216495408 | U | 5/2022 |
| JP | 4559630 | B2 | 7/2010 |
| WO | 2008076712 | A2 | 6/2008 |
| WO | 2016090023 | A1 | 6/2016 |

OTHER PUBLICATIONS

First Office Action for Chinese Application No. 202111355495.6 mailed Jul. 8, 2022.
International Search Report and Written Opinion for International Application No. PCT/CN2022/095130 mailed Aug. 9, 2022.
Extended European Search Report issued in EP Application No. 22894201.7 on Apr. 8, 2025 (11 pages).

Obtaining an input instruction at least including a set value of an opening length of the sampling window Determining an axial movement distance of the inner cutter tube according to the opening length of the sampling window Calculating the number of rotations of the motor corresponding to the axial movement distance of the inner cutter tube Controlling the motor to rotate and detecting the number of rotations of the motor Controlling the motor to stop after the motor rotates for the corresponding number of rotations

FIG. 1

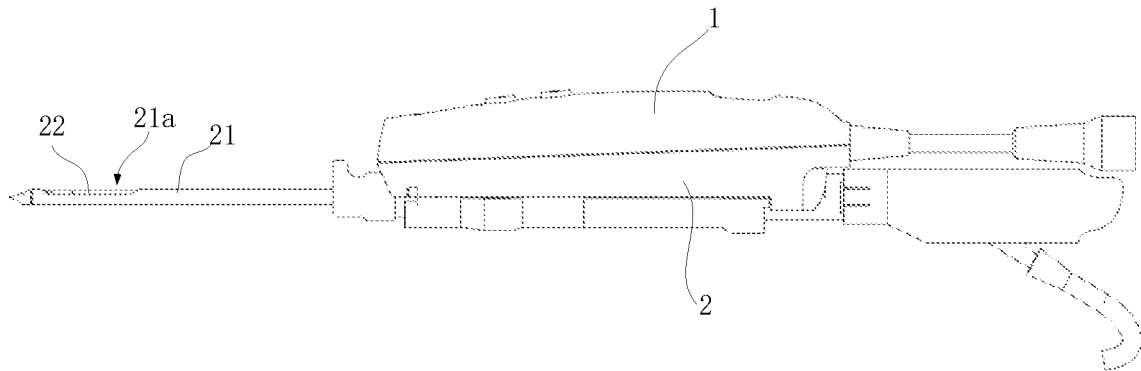

FIG. 2

METHOD AND CONTROL DEVICE FOR ADJUSTING OPENING SIZE OF SAMPLING WINDOW OF BIOPSY SURGICAL DEVICE

CROSS-REFERENCE TO RELATED APPLICATIONS

This application is a U.S. national stage application of PCT international application No. PCT/CN2022/095130 filed on May 26, 2022, which claims priority to Chinese patent application No. 2021113554956 filed with the Chinese Patent Office on Nov. 16, 2021, entitled "WINDOW OPENING SIZE ADJUSTMENT METHOD FOR SAMPLING WINDOW OF BIOPSY SURGICAL DEVICE AND CONTROL DEVICE", the entire contents of which are incorporated, in its entirety, by this reference.

TECHNICAL FIELD

The present application relates to the technical field of medical devices, and particularly to a method and control device for adjusting an opening size of a sampling window of a biopsy surgical device.

BACKGROUND

Biopsy is a technique that removes diseased tissue from the patient's body for pathological examination by cutting, clamping, or puncturing for diagnosis and treatment needs. Biopsy surgical devices are used to sample biological tissue from the human body. A widely used biopsy surgical device is the one that performs sampling through rotational cutting, which typically includes a cutter and a handle. The cutter includes an inner cutter tube and an outer cutter tube that are sleeved. The front end of the outer cutter tube is a tip for puncture. A sampling slot is defined on the side of the outer cutter tube near the front end. The front end of the inner cutter tube includes a cutting edge. During puncture, the inner cutter tube is located at the forefront and closes the sampling slot. When the puncture is in position, the inner cutter tube moves backward to expose the sampling slot. The tissue is sucked into the sampling slot under negative pressure. At this time, the inner cutter tube moves forward and performs rotational cutting, thereby cutting off the tissue entering the sampling slot and accommodating it into the front end of the inner cutter tube.

During the surgery, it is necessary to accurately control the opening size of the sampling slot according to the amount of sampling.

SUMMARY

A method for adjusting an opening size of a sampling window of a biopsy surgical device is provided. The biopsy surgical device includes a motor, an outer cutter tube, and an inner cutter tube. The outer cutter tube is sleeved over the inner cutter tube. A sampling window is defined on a side of a front end of the outer cutter tube. The motor is configured to drive the inner cutter tube to move axially through a transmission mechanism and control a front end of the inner cutter tube to stop at any position along an axial direction of the sampling window of the outer cutter tube, such that adjusting an opening length of the sampling window.

The method for adjusting the opening size of the sampling window includes obtaining an input instruction at least including a set value of an opening length of the sampling window, determining an axial movement distance of the inner cutter tube according to a current position of the inner cutter tube and the set value of the opening length of the sampling window, calculating a number of rotations of the motor corresponding to the axial movement distance of the inner cutter tube according to a transmission relationship of the transmission mechanism, and controlling the motor to rotate according to the number of rotations, causing the inner cutter tube to move axially, so that the sampling window reaches a target window opening length.

In some embodiments, when the current position of the inner cutter tube is an initial position where the front end of the inner cutter tube closes the sampling window, the axial movement distance of the inner cutter tube is determined as $L=S_1+L_0$.

When the current position of the inner cutter tube is not at the initial position, the axial movement distance of the inner cutter tube is determined as $L=S_1+(L_0-L_n)$ when $L_n \leq L_0$, and the axial movement distance of the inner cutter tube is determined as $L=S_1-(L_n-L_0)$ when $L_n \geq L_0$.

Where $S_1$ is the set value of the opening length of the sampling window, $L_0$ is a distance from the front end of the inner cutter tube to a front end of the sampling window when the inner cutter tube is located at the initial position, and $L_n$ is a distance from the front end of the inner cutter tube to the initial position.

In some embodiments, the transmission mechanism includes a transmission member fixedly connected to an output end of the motor. The transmission member includes a first thread segment. The inner cutter tube includes a second thread segment that threadedly engaged with the first thread segment. The motor drives the transmission member to rotate, which in turn drives the inner cutter tube to move axially.

In some embodiments, the transmission mechanism includes a transmission member fixedly connected to an output end of the motor. The transmission member includes a first thread segment. The transmission mechanism also includes a transmission sleeve fixedly sleeved on the inner cutter tube. The transmission sleeve and the inner cutter tube are arranged to be axially fixed and circumferentially rotate relative to each other. The transmission sleeve is provided with a second thread segment that is threadedly engaged with the first thread segment. The motor drives the transmission member to rotate, which in turn drives the inner cutter tube to move axially.

In some embodiments, the number X of rotations of the motor corresponding to the axial movement distance L of the inner cutter tube is calculated according to the following method:

$$X = \frac{L}{P},$$

where P is a pitch of the first thread segment or the second thread segment.

In some embodiments, the transmission mechanism comprises a first driving gear and a first driven gear that mesh with each other, the first driving gear is mounted on an output shaft of the motor, the inner cutter tube comprises a third thread segment, the first driven gear comprises a fourth thread segment, the first driven gear and the inner cutter tube are threadedly engaged, and the motor drives the first driving gear to rotate so that the first driven gear drives the inner cutter tube to move axially.

In some embodiments, the number X of rotations of the motor corresponding to the axial movement distance L of the inner cutter tube is calculated according to the following method:

$$X = \frac{L}{P_1 \dfrac{B}{D}},$$

where $P_1$ is a pitch of the third thread segment or the fourth thread segment, B is a number of teeth of the first driving gear, and D is a number of teeth of the first driven gear.

In some embodiments, the transmission mechanism includes a first transmission structure and a second transmission structure. The second transmission structure is configured to drive the inner cutter tube to rotate around an axis thereof. An output portion of the first transmission structure is sleeved on the inner cutter tube and is threaded with the inner cutter tube. The output portion and the inner cutter tube rotate in a same direction. There is a speed difference between the output portion and the inner cutter tube. The inner cutter tube is driven to move axially by the speed difference and thread structures on the output portion and the inner cutter tube.

In some embodiments, the first transmission structure includes a first driving gear and a first driven gear that mesh with each other. The first driving gear is arranged on an output shaft of the motor. The inner cutter tube includes a fifth thread segment. The first driven gear includes a sixth thread segment. The first driven gear and the inner cutter tube are threadedly engaged. The second transmission structure includes a second driving gear and a second driven gear that mesh with each other. The second driving gear is arranged on the output shaft of the motor. The second driven gear is sleeved on the inner cutter tube and is arranged to be circumferentially fixed and axially slidable relative to the inner cutter tube.

In some embodiments, the number X of rotations of the motor corresponding to the axial movement distance L of the inner cutter tube is calculated according to the following method:

$$X = \frac{L}{P_2 \left( \dfrac{B}{D} - \dfrac{A}{C} \right)},$$

where $P_2$ is a pitch of the fifth thread segment or the sixth thread segment, B is a number of teeth of the first driving gear, D is a number of teeth of the first driven gear, A is a number of teeth of the second driving gear, and C is a number of teeth of the second driven gear.

In some embodiments, the transmission mechanism further includes a transmission sleeve fixedly sleeved on the inner cutter tube. The transmission sleeve includes outer threads. The first driven gear is sleeved on the transmission sleeve and is threadedly engaged with the transmission sleeve.

In some embodiments, an extension segment extends axially from the transmission sleeve. One end of the second driven gear is fixedly connected with a sleeve piece. The sleeve piece is sleeved on the extension segment and cooperates with the extension segment through a convex-concave structure to transmit torque. The transmission sleeve can slide axially relative to the sleeve piece to maintain torque transmission during a relative axial movement.

In some embodiments, a groove is defined in an inner wall of the sleeve piece along an axial direction of the inner cutter tube, and a protrusion corresponding to the groove is provided on the extension segment.

In some embodiments, the biopsy surgical device further includes a support housing. The inner cutter tube and the outer cutter tube are both mounted on the support housing. The support housing includes a transmission window. The first driven gear and the second driven gear partially extend out of the support housing through the transmission window.

In some embodiments, the support housing includes a positioning structure configured to axially position the first driven gear and the second driven gear.

In some embodiments, the positioning structure includes steps formed on the transmission window and an inner wall of the support housing. The steps are configured to axially position the first driven gear and the second driven gear.

In some embodiments, the inner wall of the support housing includes a plurality of convex ribs, and an outer wall of the sleeve piece is supported by the convex ribs.

In some embodiments, a shaft portion with outer threads extends axially from the first driven gear. The shaft portion inserts into the inner cutter tube and is threadedly engaged therewith.

In some embodiments, the number of rotations of the motor is detected by a Hall sensor.

In some embodiments, the minimum unit for adjusting the opening length of the sampling window along the axial direction is E. The value of the minimum unit E ranges from 0.1 mm to 2 mm. The values of the minimum units E on the same biopsy surgical device are same.

A control device for adjusting an opening size of a sampling window of a biopsy surgical device includes an obtaining module, a distance calculation module, a rotation number calculation module, and a control module. The obtaining module is configured to acquire an input instruction. The input instruction at least includes a set value of an opening length of the sampling window. The distance calculation module is configured to determine an axial movement distance of the inner cutter tube according to the current position of the inner cutter tube and the set value of the opening length of the sampling window. The rotation number calculation module is configured to calculate the number of rotations of the motor corresponding to the axial movement distance of the inner cutter tube according to a transmission relationship of a transmission mechanism. The control module is configured to control the motor to rotate according to the number of rotations, so that the inner cutter tube moves axially and the sampling window reaches a target opening length.

A non-transitory computer-readable storage medium with a computer program stored therein is also provided. When the computer program is executed by a processor, the steps of the method are implemented.

A biopsy surgical device includes an inner cutter tube, an outer cutter tube, a motor, and a controller. The outer cutter tube is sleeved over the inner cutter tube. A sampling window is defined on a side of a front end of the outer cutter tube. The motor is configured to drive the inner cutter tube to move axially through a transmission mechanism and control a front end of the inner cutter tube to stop at any position along an axial direction of the sampling window of the outer cutter tube, such that adjusting an opening length of the sampling window. The controller is configured to execute steps of the method in the above embodiments.

BRIEF DESCRIPTION OF THE DRAWINGS

In order to illustrate the technical solutions of the embodiments of the present application or prior art more clear, the accompanying drawings used in the description of the embodiments or prior art will be briefly introduced below. It is apparent that the accompanying drawings described herein are only some embodiments of the present application. For those of ordinary skill in the art, other drawings can also be obtained from these drawings without creative efforts.

FIG. 1 is a flow chart according to an embodiment.

FIG. 2 is a schematic structural diagram of a biopsy surgical device according to an embodiment.

DETAILED DESCRIPTION OF THE EMBODIMENTS

Figure 3:
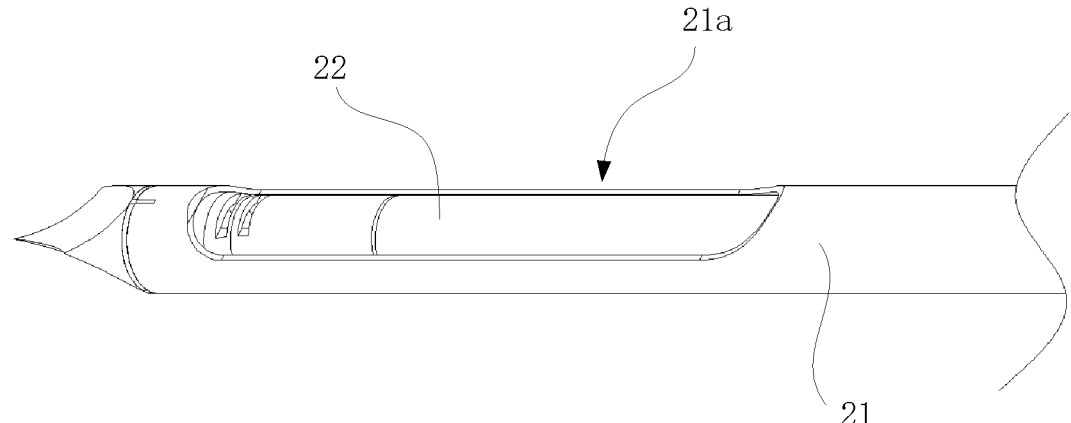
FIG. 3 is a schematic structural diagram of an outer cutter tube and an inner cutter tube according to an embodiment.
Figure 4:
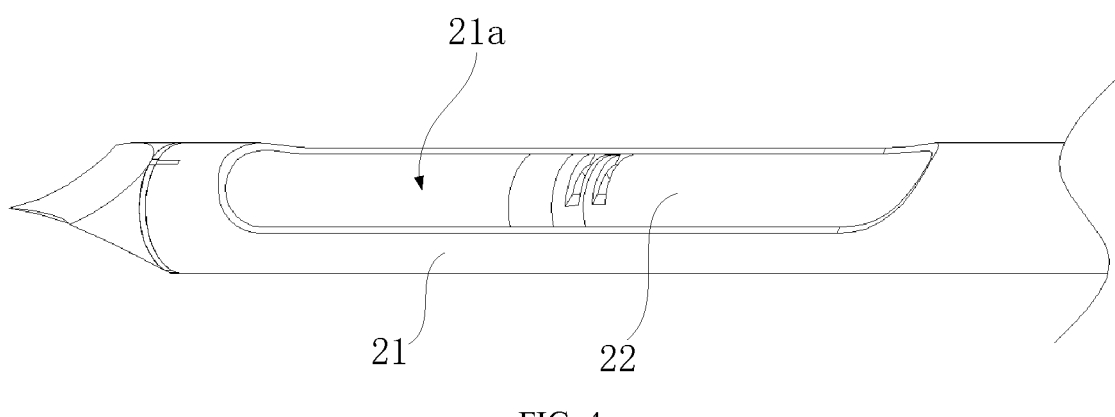
FIG. 4 is a schematic structural diagram showing an inner cutter tube exposing/covering part of a sampling window according to an embodiment.
Figure 5:
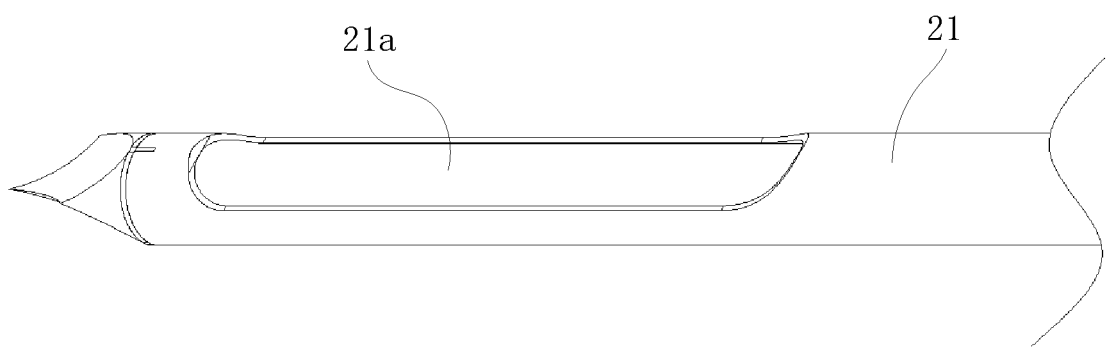
FIG. 5 is a schematic structural diagram showing a sampling window that is completely opened according to an embodiment.

The implementation of the present application is described below in conjunction with specific embodiments. Those familiar with this technology can easily know other advantages and effects of the present application from the content disclosed in the present specification.

EMBODIMENTS

In the present application, the orientation "front" and "back" are defined with reference to the usage status of the biopsy surgical device. During usage, the side facing the patient is the front, and the side away from the patient is the back.

During a biopsy surgery, the retraction position and distance of the inner cutter tube are controlled according to the amount of sampling so as to adjust the opening size of the sampling window. As known to the applicant, there are typically only 3 to 4 fixed adjustment positions, and adjustments can only be made between these fixed positions. For example, the sampling window can be opened at 50%, 100%, etc. It is impossible to achieve a refined and continuous adjustment of the opening size of the window. It only adapts to several fixed sampling lengths, resulting in poor adaptability and weak universality of the biopsy surgical device.

As shown in FIGS. 1 to 6, the present embodiment illustrates a biopsy surgical device, including a handle 1 and a cutter assembly 2 that are connected. The cutter assembly 2 includes an outer cutter tube 21 and an inner cutter tube 22 that are arranged coaxially. The front end of the outer cutter tube 21 includes a puncture tip. A sampling window 21*a* is defined on the side of the outer cutter tube 21 near the front end. The front end of the inner cutter tube 22 includes a cutting edge. The inner cutter tube 22 and the outer cutter tube 21 are sleeved. The inner cutter tube 22 is inserted in the outer cutter tube 21, or the inner cutter tube 22 is sleeved over the outer cutter tube 21. The inner cutter tube 22 can move axially relative to the outer cutter tube 21.

A motor 11 is arranged in the handle 1. The motor 11 is connected to the inner cutter tube 22 through a transmission mechanism so as to drive the inner cutter tube 22 to move along the axial direction (front and back direction) and control the front end of the inner cutter tube to stop at any position along the axial direction of the sampling window of the outer cutter tube, such that the length of the sampling window 21*a* that is exposed or covered by the inner cutter tube can be continuously adjusted, thereby adjusting the actual opening length of the sampling window 21*a* for tissue aspiration, i.e., the axial dimension of the actual used sampling window 21*a*.

During puncture, the inner cutter tube 22 is located at the forefront and closes the sampling window 21*a*. When the puncture is in position, the inner cutter tube 22 moves backward to expose the sampling window 21*a*. The tissue is sucked into the sampling window 21*a* under negative pressure. At this time, the inner cutter tube moves forward or rotates while moving forward, so as to cut off the tissue entering the sampling window 21*a* and then transport the cut tissue to a sample collection box through the inner cutter tube under atmospheric pressure. The position of the inner cutter tube 22 can be adjusted between completely covering the sampling window 21*a* (the state shown in FIG. 4) and completely exposing the sampling window 21*a* (the state shown in FIG. 5), so that the actual opening size of the sampling window 21*a* can be continuously adjusted according to the sampling requirements.

Figure 6:
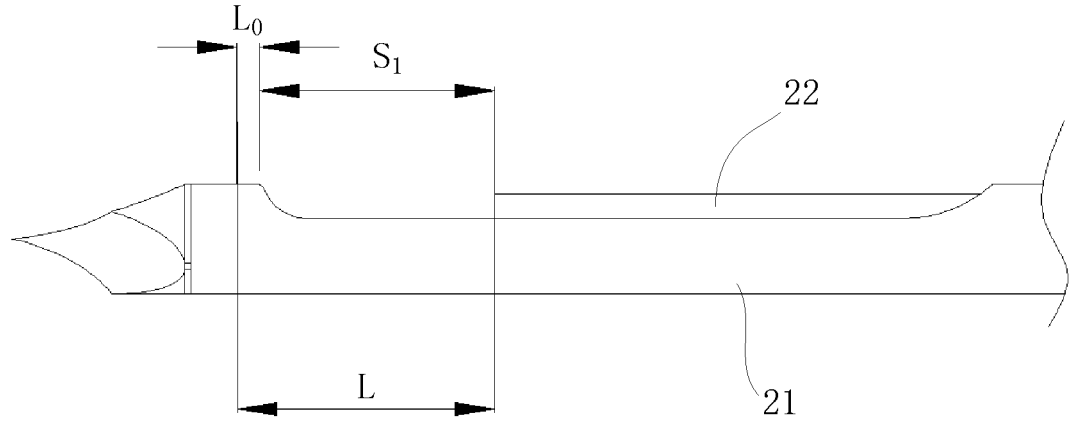
FIG. 6 is a schematic diagram showing a relationship between an opening length of a sampling window and an axial movement distance of an inner cutter tube according to an embodiment.
Figure 7:
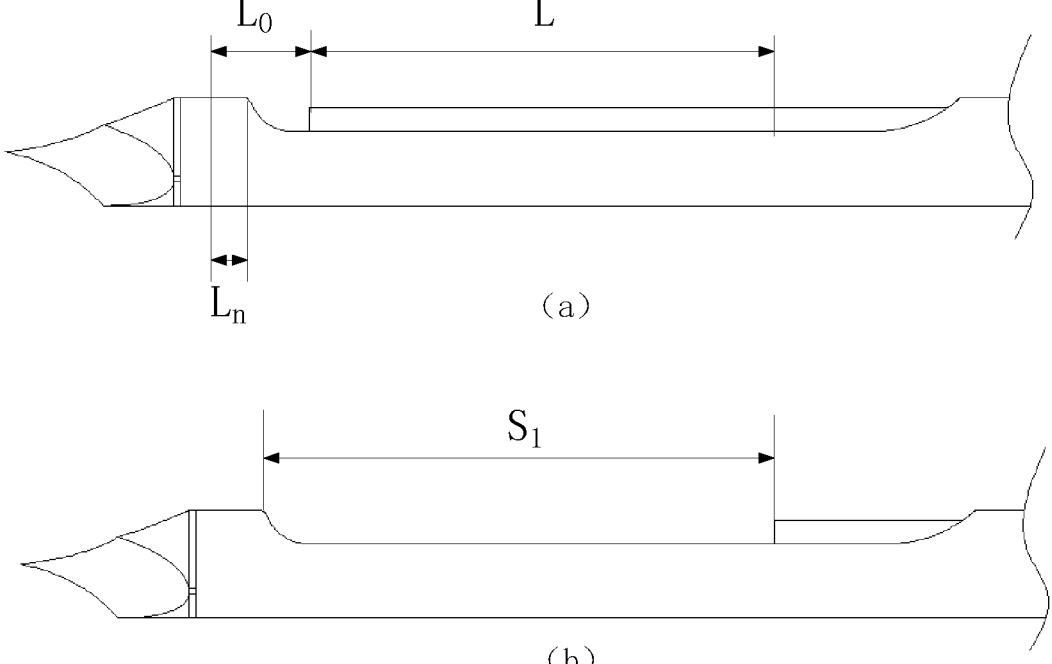
FIG. 7 is a schematic diagram showing a relationship between an opening length of a sampling window and an axial movement distance of an inner cutter tube according to another embodiment.

A method for adjusting the opening size of a sampling window of a biopsy surgical device includes obtaining an input instruction. The input instruction at least includes a set value of an opening length of the sampling window. For example, a window opening length parameter can be input through buttons or a touch screen on the handle 1. Alternatively, a relative amount of increase/decrease, i.e., an adjustment value of the window opening length, is input. The set value of the opening length of the sampling window can be calculated according to the input adjustment value. Then, an axial movement distance of the inner cutter tube 22 is determined according to the actual required window opening length, i.e., according to the current position of the inner cutter tube 22 and the set value of the opening length of the sampling window. For example, when the front end of the inner cutter tube 22 is flush with the front end of sampling window 21*a*, the distance the inner cutter tube 22 moves backward is the window opening length. When the front end of the inner cutter tube 22 is forward beyond the front end of the sampling window 21*a*, the distance the inner cutter tube 22 moves backward needs to be greater than the input window opening length, and the difference is the distance between the front end of the inner cutter tube 22 and the front end of the sampling window 21*a*. This distance (i.e., the difference) is determined when the biopsy surgical device is manufactured. The movement distance of the inner cutter tube 22 is determined according to the relative position, as shown in FIG. 6 and FIG. 7.

Then, the number of rotations of the motor corresponding to the axial movement distance of the inner cutter tube 22 is calculated according to a transmission relationship of the transmission mechanism, such that the motor is controlled to rotate according to the number of rotations, casing the inner cutter tube 22 moves axially until the sampling window 21*a* reaches the specified window opening length.

The number of rotations of the motor can be detected by a Hall sensor, and the motor stops rotating after completing the specified number of rotations.

An input device, a driver, and a Hall sensor are connected to the controller, respectively. The input device may be a button, a touch screen, etc. The controller stores a calculation method for the relationship between the axial movement distance of the inner cutter tube 22 and the number of rotations of the motor. When obtaining the input instruction from the input device, the controller calculates the distance that the inner cutter tube 22 needs to move along the axial direction according to the relative position relationship between the inner cutter tube 22 and the sampling window 21*a*. Then, the number of rotations that the motor needs to rotate is determined according to the transmission relationship of the current transmission mechanism. The driver drives the motor to rotate according to the determined number of rotations. At the same time, the Hall sensor detects the number of rotations of the motor and feeds it back to the controller. The number of rotations of the motor is obtained in real time. When the corresponding number of rotations is reached, the controller controls the motor to stop through the driver. The position of the inner cutter tube 22 can be adjusted between completely covering the sampling window 21*a* and completely exposing the sampling window, so that the actual opening length of the sampling window 21*a* can be adjusted to adapt to the needs of different sampling sizes. In addition, based on the relationship between the axial movement distance of the inner cutter tube 22 and the number of rotations of the motor, the opening length of the sampling window 21*a* can be accurately controlled and can be adjusted in real time as needed by controlling the number of motor rotations.

The controller may be a general-purpose processor, including a Central Processing Unit (CPU), a Network Processor (NP), etc. The controller may also be a Digital Signal Processor (DSP), an Application-Specific Integrated Circuit (ASIC), a Field-Programmable Gate Array (FPGA) or other programmable logic devices, a discrete gate or transistor logic device, or a discrete hardware component.

As shown in FIG. 6, when the current position of the inner cutter tube 22 is the initial position (i.e., the inner cutter tube is located at the forefront and closes the sampling window), the axial movement distance L of the inner cutter tube 22 is determined as $L=S_1+L_0$, where $S_1$ is the input set value of opening length of the sampling window, and $L_0$ is the distance from the front end of the inner cutter tube 22 to the front end of the sampling window 21*a* when the inner cutter tube 22 is at the initial position.

When the current position of the inner cutter tube 22 is not at the initial position, there are two cases. When $L_n \leq L_0$, it means that the inner cutter tube 22 is located between the initial position and the front end of the sampling window 21*a*. The axial movement distance L of the inner cutter tube

22 is determined as $L=S_1+(L_0-L_n)$, and the distance to be moved is greater than the set value. When $L_n \geq L_0$, it means that the inner cutter tube 22 is located behind the front end of the sampling window 21*a*, the distance to be moved is less than the set value, and $L=S_1-(L_n-L_0)$. $L_n$ is the distance from the front end of the inner cutter tube 22 to the initial position. The inner cutter tube 22 moves backward when L>0, and the inner cutter tube 22 moves forward when L<0.

As shown in FIG. 7, (a) shows the current position of the inner cutter tube 22, and (b) shows the final adjustment position of the inner cutter tube 22. The current position of the inner cutter tube 22 is behind the front end of the sampling window 21*a*, and the axial movement distance of the inner cutter tube 22 is $L=S_1-(L_n-L_0)$. The calculation method is similar when $L_n \leq L_0$.

Regarding the transmission structure of the biopsy surgical device, there are different transmission ratio calculation methods according to different transmission structures.

In an embodiment, the output end of the motor 11 and the inner cutter tube 22 are directly connected through threads, and the inner cutter tube 22 moves axially. When the motor 11 completes one revolution, the inner cutter tube 22 moves axially by one pitch P. The number X of rotations of the motor corresponding to the axial movement distance L of the inner cutter tube 22 is obtained by $$X = \frac{L}{P},$$

where P is the pitch of the thread of the inner cutter tube 22 that matches the output end of the motor 11. When X>0, the motor rotates forward and the inner cutter tube 22 moves backward. When X<0, the motor rotates in reverse and the inner cutter tube 22 moves forward. X is not necessarily an integer, in other words, the motor can rotate half a turn or a quarter of a turn. The number of rotations of the motor can be set according to actual needs.

Figure 8:
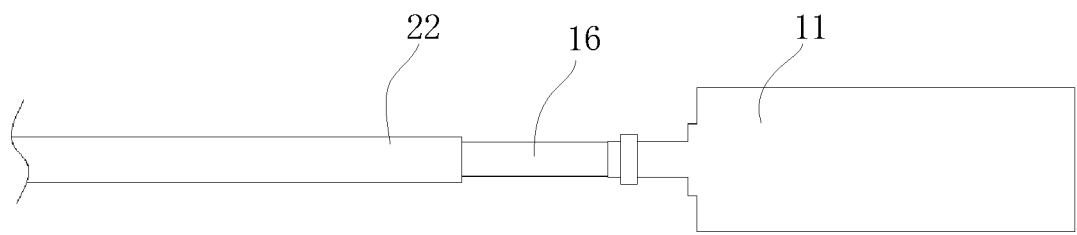
FIG. 8 is a schematic diagram showing a transmission of an inner cutter tube according to an embodiment.

Specifically, as shown in FIG. 8, the output end of the motor 11 is fixedly connected to a transmission member 16 that rotates synchronously with it. The transmission member 16 includes a first thread segment. The first thread segment may be an inner screw thread or an outer screw thread. The back portion of the inner cutter tube 22 includes a second thread segment that matches the first thread segment, and P is the pitch of the first thread segment or the second thread segment. The transmission member 16 is directly threaded with the back portion of the inner cutter tube 22. A limiting element is set on the cutter assembly or the handle to limit the rotation of the inner cutter tube 22 so that the inner cutter tube 22 moves axially.

Figure 9:
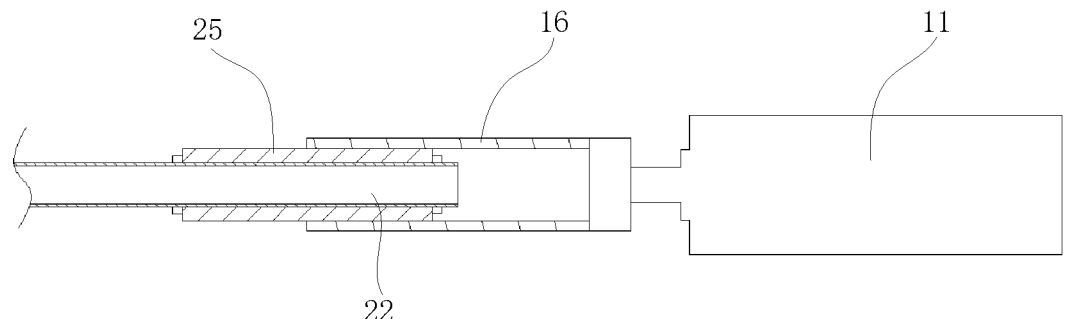
FIG. 9 is a schematic diagram showing a transmission of an inner cutter tube according to another embodiment.

As shown in FIG. 9, in another embodiment, the output end of the motor 11 is fixedly connected to a transmission member 16 that rotates synchronously with it. The transmission member 16 includes a first thread segment. The first thread segment may be an inner screw thread or an outer screw thread. A transmission sleeve 25 is arranged on the inner cutter tube 22. The transmission sleeve 25 includes a second thread segment that matches the first thread segment. The transmission member 16 and the transmission sleeve 25 are in a threaded connection. The transmission sleeve 25 and the inner cutter tube 22 are arranged to be axially fixed and circumferentially rotate relative to each other, so that when the motor 11 rotates, the inner cutter tube 22 is driven to move axially through the transmission sleeve 25, and the front end of the inner cutter tube 22 can stop at any position along the axial direction of the sampling window 21*a* of the outer cutter tube 21. This embodiment is applicable for the biopsy surgical device in which the inner cutter tube 22 does not rotate but only moves axially. A limiting element may be set on the cutter assembly or the handle to limit the rotation of the inner cutter tube 22.

Figure 10:
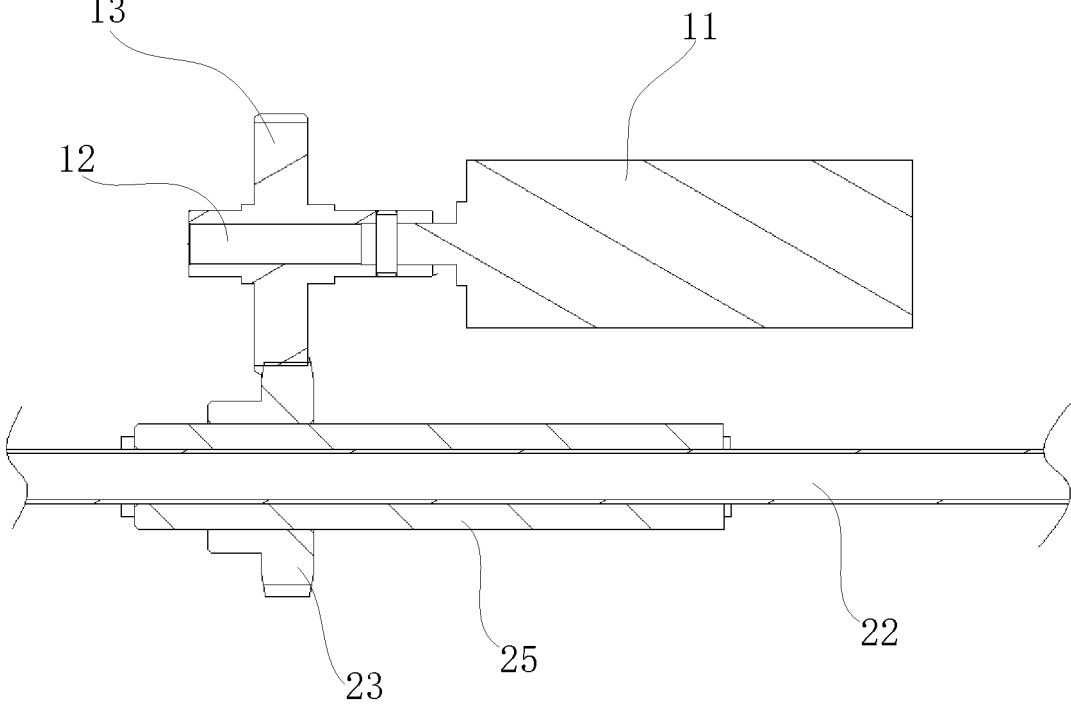
FIG. 10 is a schematic diagram showing a transmission of an inner cutter tube according to yet another embodiment.

As shown in FIG. 10, in an embodiment, the transmission mechanism includes a first driving gear 13 and a first driven gear 23 that mesh with each other. The output end of the motor 11 is connected with an output shaft 12. The first driving gear 13 is sleeved on the output shaft 12 and rotates with the output shaft 12. The inner cutter tube 22 includes an outer thread segment (i.e., a third thread segment). The inner wall of the first driven gear 23 includes inner threads (i.e., a fourth thread segment). The first driven gear 23 is sleeved on the outer thread segment of the inner cutter tube 22 and is threadedly engaged with the inner cutter tube 22. By the cooperation of the threaded pair, the inner cutter tube 22 is driven to move axially. The first motor 11 drives the first driving gear 13 to rotate, causing the first driven gear 23 to drive the inner cutter tube 22 to move axially and stop the front end of the inner cutter tube 22 at any position in the axial direction of the sampling window 21*a* of the outer cutter tube 21, thereby changing the size of the sampling window 21*a* exposed or covered by the inner cutter tube 21.

In this embodiment, to facilitate manufacturing, the transmission sleeve 25 is fixedly sleeved on the inner cutter tube 22. The transmission sleeve 25 is provided with outer threads to cooperate with the first driven gear 23. In other embodiments, a shaft portion with outer threads extends axially from the first driven gear 23. The shaft portion inserts into the inner cutter tube 22 and is threadedly engaged therewith.

The above embodiment is applicable for the biopsy surgical device in which the inner cutter tube 22 rotates while cutting, and for the biopsy surgical device in which the inner cutter tube 22 does not rotate but only moves axially.

In the above structure, by the transmission of the gear set and the threads, after the first driven gear 23 rotates one turn, the inner cutter tube 22 moves axially by one pitch, and the motor 11 rotates D/B turns, then the number X of rotations of the motor 11 corresponding to the axial movement distance L of the inner cutter tube 22 is obtained by $$X = \frac{L}{P_1 \frac{B}{D}},$$

where $P_1$ is the pitch of the third thread segment or the fourth thread segment, B/D is the transmission ratio between the first driving gear 13 and the first driven gear 23, for example, B is the number of teeth of the first driving gear, and D is the number of teeth of the first driven gear.

Figure 11:
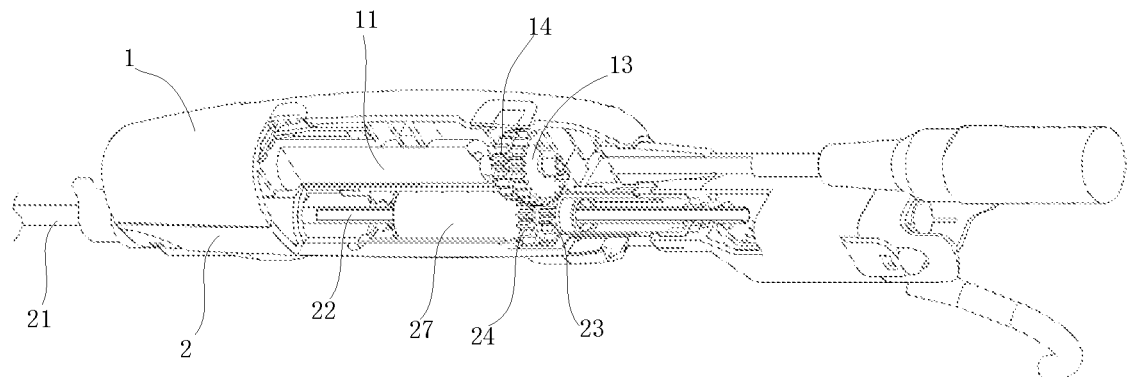
FIG. 11 is a schematic diagram showing a transmission of an inner cutter tube according to yet another embodiment.

As shown in FIG. 11, in an embodiment, the transmission mechanism includes a first transmission structure and a second transmission structure. The motor drives the inner cutter tube 22 to rotate around the axis thereof through the second transmission structure. An output portion of the first transmission structure is sleeved on the inner cutter tube 22 and is threadedly engaged with the inner cutter tube 22. The output portion and the inner cutter tube 22 rotate in the same direction, and there is a speed difference between the output portion and the inner cutter tube 22. The inner cutter tube 22 is driven to move axially by the speed difference and the threaded structure. Therefore, a slower movement adjustment in the axial direction is achieved while the inner cutter tube 22 rotates at a high speed, which facilitates precise adjustment.

Figure 12:
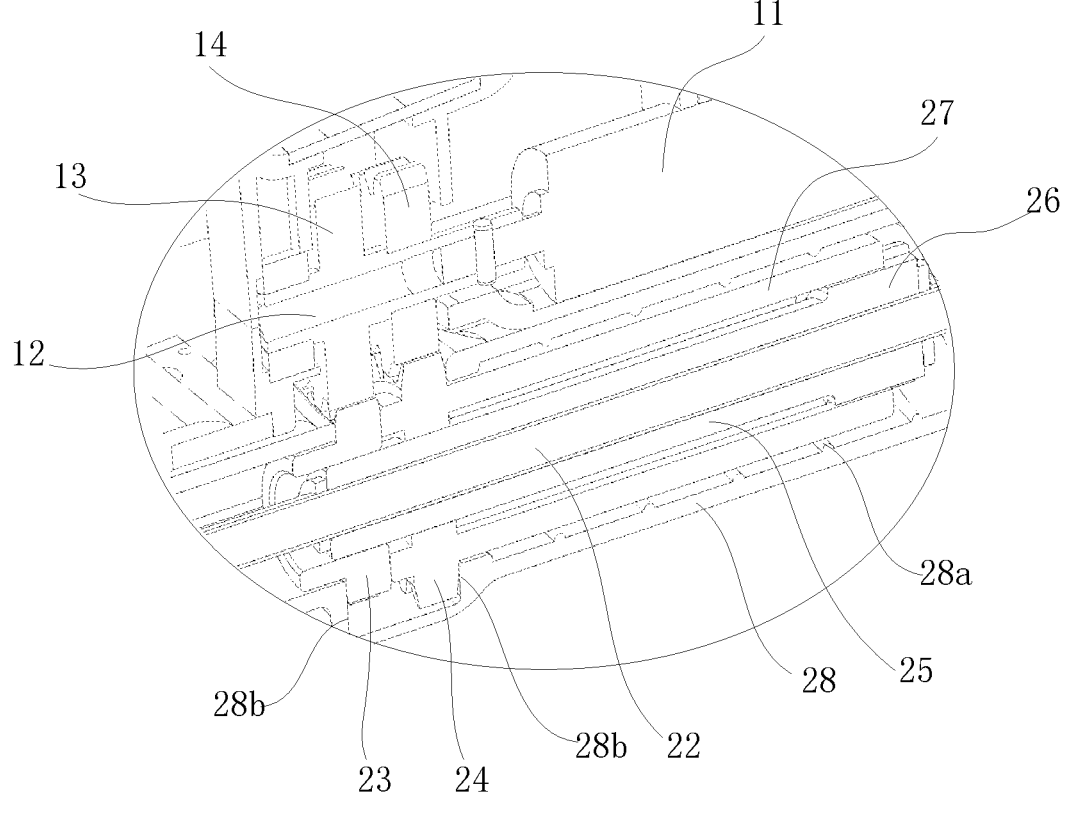
FIG. 12 is a partially enlarged view of FIG. 11.

As shown in FIG. 11 and FIG. 12, the first transmission structure includes a first driving gear 13 and a first driven gear 23 that mesh with each other. The first driven gear 23 is the output portion of the first transmission structure. The output end of the motor 11 is connected with an output shaft 12. The first driving gear 13 is sleeved on the output shaft 12 and rotates with the output shaft 12. The inner cutter tube 22 includes an outer thread segment (a fifth thread segment), and the inner wall of the first driven gear 23 includes inner threads (a sixth thread segment). The first driven gear 23 is sleeved on the outer thread segment of the inner cutter tube 22 and is threadedly engaged with the inner cutter tube 22.

Torque is transmitted between the motor 11 and the inner cutter tube 22 through the second transmission structure to drive the inner cutter tube 22 to rotate. The second transmission structure includes a second driving gear 14 and a second driven gear 24 that mesh with each other. The second driving gear 14 is arranged on the output shaft 12 of the motor 11 and rotates synchronously with the output shaft 12. The second driven gear 24 is coaxially sleeved on the inner cutter tube 22 and is arranged to be circumferentially fixed and axially slidable relative to the inner cutter tube 22. In other words, the inner cutter tube 22 rotates with the second driven gear 24, but the inner cutter tube 22 can slide axially relative to the second driven gear 24 and still transmit torque during sliding.

Specifically, the transmission mechanism also includes a transmission sleeve 25 fixedly sleeved on the inner cutter tube 22. The transmission sleeve 25 includes outer threads. The first driven gear 23 is sleeved on the transmission sleeve 25 and is threadedly engaged with the transmission sleeve 25.

In the above structure, the inner cutter tube 22 is driven by the transmission mechanism to rotate around the axis thereof, i.e., rotate synchronously with the second driven gear 24. At the same time, the first driven gear 23 is threadedly engaged with the inner cutter tube 22, and the inner cutter tube 22 and the first driven gear rotate in the same direction but at different speeds. There is a speed difference, which drives the inner cutter tube 22 to move axially through the threads.

In an embodiment, an extension segment 26 extends axially from the transmission sleeve 25. One end of the second driven gear 24 is fixedly connected with a sleeve piece 27. The sleeve piece 27 is sleeved on the extension segment 26 and cooperates with the extension section 26 through a convex-concave structure to transmit torque. In addition, the transmission sleeve 25 can slide axially relative to the sleeve piece 27 to maintain torque transmission during the relative axial movement.

Figure 13:
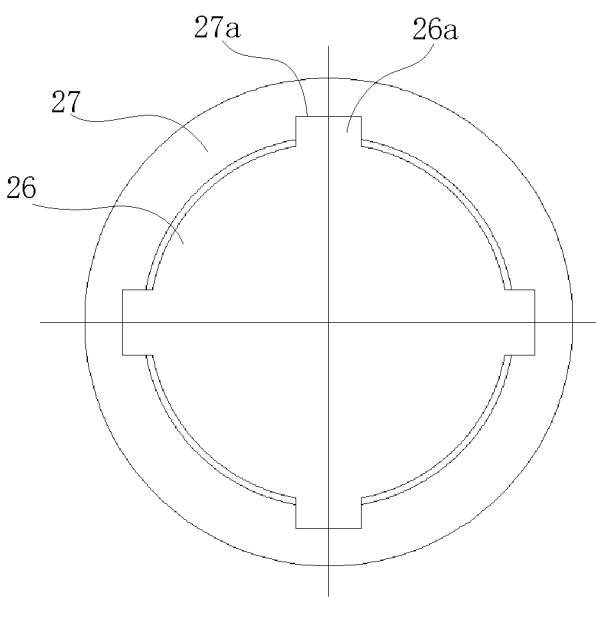
FIG. 13 is an axial view showing the mating of a sleeve piece with an extension section according to an embodiment.

As shown in FIG. 13, in an embodiment, a groove 27*a* is defined in the inner wall of the sleeve piece 27 along the axial direction of the inner cutter tube 22. Specifically, a plurality of grooves 27*a* are distributed along the circumferential direction. Protrusions 26*a* corresponding to the grooves 27*a* are provided on the extension segment 26, and the length of the groove 27*a* along the axial direction of the inner cutter tube 22 is greater than or less than the length of the protrusion 26*a* along the axial direction of the inner cutter tube 22. Alternatively, the extension segment 26 and the sleeve piece 27 may also be matched by keyway or spline.

In this embodiment, the cutter assembly 2 also includes a support housing 28. The inner cutter tube 22 and the outer cutter tube 21 are both mounted on the support housing 28. The support housing 28 includes a transmission window. The first driven gear 23 and the second driven gear 24 partially extend out of the support housing 28 through the transmission window. The support housing 28 includes a positioning structure configured to axially position the first driven gear 23 and the second driven gear 24, so that the first driven gear 23 and the second driven gear 24 are fixed in the axial direction and only perform rotational movement. In this embodiment, the axial positioning is achieved by the steps 28b formed by the inner wall of the support housing 28 and the transmission window. In order to reduce friction while ensuring support, a plurality of convex ribs 28a are provided on the inner wall of the support housing 28, and the outer wall of the sleeve piece 27 is supported by the convex ribs 28a.

Based on the above transmission structure, the process of calculating the number of rotations of the motor according to the axial movement distance L of the inner cutter tube 22 is as follows.

The first driving gear 13 and the second driving gear 14 are both connected to the output shaft of the motor and rotate at the same speed. The number of teeth on the first driving gear 13, the second driving gear 14, the first driven gear 23, and the second driven gear 24 are different, resulting in different transmission ratios for the two gear sets. Therefore, the speeds of the first driven gear 23 and the second driven gear 24 are different, and the speed of the second driven gear 24 is the same as that of the inner cutter tube 22 rotating around the axis thereof.

The speed difference between the first driven gear 23 and the second driven gear 24 is $N_1$:

$$N_1 = \frac{B}{D}N - \frac{A}{C}N = \left(\frac{B}{D} - \frac{A}{C}\right)N$$

where N is the speed of the first driving gear 13 and the second driving gear 14, $$\left(\frac{B}{D} - \frac{A}{C}\right)$$

is the speed difference coefficient. B/D is the transmission ratio between the first driving gear 13 and the first driven gear 23, which may be a ratio of the number of teeth of the gears, or the reciprocal of the radius ratio. A/C is the transmission ratio between the second driving gear 14 and the second driven gear 24, which may be the ratio of the number of teeth of the gears, or the reciprocal of the radius ratio.

From the above formula, it can be seen that the first driven gear 23 rotates faster than the second driven gear 24 by $N_1$. The transmission sleeve 25 and the second driven gear 24 rotate synchronously and have the same rotation speed, i.e., the first driven gear 23 rotates faster than the transmission sleeve 25 by $N_1$. Since the second driven gear 24 and the first driven gear 23 are axially fixed, the speed difference between the first driven gear 23 and the transmission sleeve 25 causes the transmission sleeve 25 to move forward or backward through the thread of the first driven gear 23 (the forward or backward movement is achieved by changing the rotation direction of the motor). Due to the axial fixation between the inner cutter tube 22 and the transmission sleeve 25, the forward or backward movement of the inner cutter tube 22 is achieved.

The speed of the first driven gear 23 may be higher than or lower than the speed of the second driven gear 24. The speed of the driven gears and the rotation direction of the motor jointly determine whether the inner cutter tube 22 moves forward or backward.

The output speed $N_2$ of the inner cutter tube 22 is as follows:

$$N_2 = \frac{A}{C}N,$$

which is the same as the speed of the second driven gear 24.

The speed of forward and backward movement of the inner cutter tube 22 is related to the speed difference between the two driven gears and the pitch of the thread. The feed rate V of the inner cutter tube 22 is as follows:

$$V = \frac{N_1 \times P_2}{60},$$

where $P_2$ is the pitch of the outer thread of the transmission sleeve 25 or the pitch of the inner thread of the first driven gear 23. The transmission sleeve 25 has the same pitch as the first driven gear 23.

When the first driven gear 23 rotates one turn relative to the second driven gear 24, the inner cutter tube 22 moves forward by one pitch P. Since the speed difference coefficient between the first driven gear 23 and the second driven gear 24 is $$\left(\frac{B}{D} - \frac{A}{C}\right),$$

the second driving gear 14, the first driving gear 13, and the motor all rotate Y turns, where $$Y = 1 / \left(\frac{B}{D} - \frac{A}{C}\right).$$

The first driven gear 23 and the second driven gear 24 are one turn apart, and the inner cutter tube 22 moves forward by pitch $P_2$.

When the axial movement distance of the inner cutter tube 22 is L, the second driving gear 14, the first driving gear 13, and the motor all rotate X circles, then $$\frac{P_2}{Y} = \frac{L}{X} \text{ and } X = \frac{L}{P_2\left(\frac{B}{D} - \frac{A}{C}\right)}.$$

The first driven gear 23 rotates $$\frac{B}{D}X$$

turns, and the second driven gear 24 rotates $$\frac{A}{C}X$$

turns. Therefore, in the case that the axial movement distance of the inner cutter tube 22 is known, the corresponding number of rotations of the motor can be calculated. By counting with a Hall sensor, the motor stops rotating after the specified number of rotations is reached. When there are multiple stages of gear transmission, the transmission ratio can be calculated in a similar way.

To facilitate the doctor's intuitive operation, the minimum unit for adjusting the opening length of the sampling window 21*a* along the axial direction is E, i.e., the inner cutter tube 22 can be moved along the axial direction by one minimum unit E at a time. The value of the minimum unit E ranges from 0.1 mm to 2 mm, such as 0.1 mm, 1 mm, 1.5 mm, 2 mm, etc. It is possible to move several minimum units in succession. For example, when the minimum adjustment unit of the window opening length of a biopsy surgical device is 0.1 mm, each movement can increase or decrease by 0.1 mm, and several 0.1 mm can be continuously increased or decreased. The minimum unit of each biopsy surgical device has a unique value. The distance of each movement is the same, achieving a continuous and fine adjustment of the movement distance, so as to achieve a continuous adjustment of the actual opening length of the sampling window 21*a*.

During the adjustment process, the final parameter of the window opening length, such as 25 mm, may be directly input. Alternatively, incremental parameters may be input, such as increasing or decreasing 5 mm on the basis of the original window opening length.

During the operation of the biopsy surgical device, before and during puncture, the inner cutter tube 22 moves to the frontmost position to close the sampling window 21*a*. After the puncture is in place, the motor 11 drives the inner cutter tube 22 to move backward according to the sampling size requirement until the actual opening length of the sampling window 21*a* corresponds to the input value. Then, the tissue is sucked into the sampling window 21*a* from the back end of the inner cutter tube 22 through a negative pressure device. After this, the inner cutter tube 22 is driven to move forward and rotate at a high speed to cut off the tissue and accommodate it at the front end of the inner cutter tube 22, and the sampling is completed.

In this embodiment, the position of the inner cutter tube 22 can be continuously adjusted between completely covering the sampling window 21*a* and completely exposing the sampling window 21*a*, thereby adjusting the actual opening length of the sampling window 21*a*, and achieving continuous forward and backward adjustment of the inner cutter tube 22. Therefore, the opening length of the sampling window 21*a* can be adjusted in real time and continuously according to the sampling requirements, so as to meet precise resection needs of different sizes of lesions. In specific embodiments, the minimum opening can be only 5 mm, which meets the needs for precise resection of tiny lesions and preserves surrounding normal tissues to the greatest extent. The maximum opening can reach 30 mm, allowing for a larger sample size to be obtained in a single resection, improving resection efficiency, reducing surgical time, and meeting the surgical needs of larger lesions.

In an embodiment, a control device for adjusting an opening size of a sampling window of a biopsy surgical device includes an obtaining module, a distance calculation module, a rotation number calculation module, and a control module. The obtaining module is configured to obtain input instructions, which at least include a setting value of a sampling window opening length. The distance calculation module is configured to determine an axial movement distance of the inner cutter tube according to the current position of the inner cutter tube and the set value of the opening length. The rotation number calculation module is configured to calculate the number of rotations of the motor corresponding to the axial movement distance of the inner cutter tube according to a transmission relationship of the transmission mechanism. The control module is configured to control the motor to rotate according to the number of rotations, causing the inner cutter tube to move axially and achieving the target opening length of the sampling window.

Specific features of the control device for adjusting an opening size of a sampling window of a biopsy surgical device can be referred to the features of the method for adjusting an opening size of a sampling window of a biopsy surgical device, which will not be repeated here. The modules in the above-mentioned control device for adjusting an opening size of a sampling window of a biopsy surgical device may be implemented in whole or in part by software, hardware, and combinations thereof. Each of the above modules may be embedded in or independent of a processor of a computer device in a form of hardware, or may be stored in a memory of the computer device in a form of software, so as to be called by the processor to perform the operations corresponding to the above modules. It should be noted that the division of modules in the embodiments of the present application is schematic and is only a logical function division. In actual implementation, there may be other division manners.

In an embodiment, a non-transitory computer-readable storage medium is provided, in which a computer program is stored. The computer program, when executed by a processor, the steps of the methods in the above embodiments are implemented.

Anyone familiar with this technology can modify or change the above embodiments without departing from the spirit and scope of the present application. Therefore, all equivalent modifications or changes made by those skilled in the art without departing from the spirit and technical ideas disclosed in the present application shall be covered by the claims of the present application.

What is claimed is:

1. A method for adjusting an opening size of a sampling window of a biopsy surgical device, the biopsy surgical device comprising a motor, an outer cutter tube, and an inner cutter tube, the outer cutter tube being sleeved over the inner cutter tube, the sampling window being defined on a side of a front end of the outer cutter tube, the motor being configured to drive the inner cutter tube to move axially through a transmission mechanism and control a front end of the inner cutter tube to stop at any position along an axial direction of the sampling window of the outer cutter tube, thereby adjusting an opening length of the sampling window;

the method comprising:

obtaining an input instruction which at least comprises a set value of an opening length of the sampling window;

determining an axial movement distance of the inner cutter tube according to a current position of the inner cutter tube and the set value of the opening length of the sampling window;

15

16 calculating a number of rotations of the motor corresponding to the axial movement distance of the inner cutter tube according to a transmission relationship of the transmission mechanism; and controlling the motor to rotate according to the number of rotations, causing the inner cutter tube to move axially, so that the sampling window reaches a target window opening length.

2. The method according to claim 1, wherein:

when the current position of the inner cutter tube is an initial position where the front end of the inner cutter tube closes the sampling window, the axial movement distance of the inner cutter tube is determined as $L=S_1+L_0$;

when the current position of the inner cutter tube is not at the initial position, the axial movement distance of the inner cutter tube is determined as $L-S_1+(L_0-L_n)$ when $L_n \leq L_0$, and the axial movement distance of the inner cutter tube is determined as $L=S_1-(L_n-L_0)$ when $L_n \geq L_0$;

where $S_1$ is the set value of the opening length of the sampling window, $L_0$ is a distance from the front end of the inner cutter tube to a front end of the sampling window when the inner cutter tube is located at the initial position, and $L_n$ is a distance from the front end of the inner cutter tube to the initial position.

3. The method according to claim 1, wherein the transmission mechanism comprises a transmission member fixedly connected to an output end of the motor, the transmission member comprises a first thread segment, the inner cutter tube comprises a second thread segment that threadedly engaged with the first thread segment, and the motor drives the transmission member to rotate, which in turn drives the inner cutter tube to move axially, wherein the number X of rotations of the motor corresponding to the axial movement distance L of the inner cutter tube is calculated according to the following method:

$$X = \frac{L}{P}$$

where P is a pitch of the first thread segment or the second thread segment.

4. The method according to claim 1, wherein the transmission mechanism comprises a transmission member fixedly connected to an output end of the motor, the transmission member comprises a first thread segment, the transmission mechanism also comprises a transmission sleeve fixedly sleeved on the inner cutter tube, the transmission sleeve and the inner cutter tube are arranged to be axially fixed and circumferentially rotate relative to each other, the transmission sleeve is provided with a second thread segment that is threadedly engaged with the first thread segment, and the motor drives the transmission member to rotate, which in turn drives the inner cutter tube to move axially;

wherein the number X of rotations of the motor corresponding to the axial movement distance L of the inner cutter tube is calculated according to the following method, $$X = \frac{L}{P}$$

where P is a pitch of the first thread segment or the second thread segment.

5. The method according to claim 1, wherein the transmission mechanism comprises a first driving gear and a first driven gear that mesh with each other, the first driving gear is mounted on an output shaft of the motor, the inner cutter tube comprises a third thread segment, the first driven gear comprises a fourth thread segment, the first driven gear and the inner cutter tube are threadedly engaged, and the motor drives the first driving gear to rotate so that the first driven gear drives the inner cutter tube to move axially;

wherein the number X of rotations of the motor corresponding to the axial movement distance L of the inner cutter tube is calculated according to the following method:

$$X = \frac{L}{P_1 \dfrac{B}{D}}$$

where $\mu_1$ is a pitch of the third thread segment or the fourth thread segment, B is a number of teeth of the first driving gear, and D is a number of teeth of the first driven gear.

6. The method according to claim 1, wherein the transmission mechanism comprises a first transmission structure and a second transmission structure, the second transmission structure is configured to drive the inner cutter tube to rotate around an axis thereof, an output portion of the first transmission structure is sleeved on the inner cutter tube and is threaded with the inner cutter tube, the output portion and the inner cutter tube rotate in a same direction, the output portion and the inner cutter tube are configured with a speed difference therebetween, and the inner cutter tube is driven to move axially by the speed difference and thread structures on the output portion and the inner cutter tube.

7. The method according to claim 6, wherein the first transmission structure comprises a first driving gear and a first driven gear that mesh with each other, the first driving gear is arranged on an output shaft of the motor, the inner cutter tube comprises a fifth thread segment, the first driven gear comprises a sixth thread segment, the first driven gear and the inner cutter tube are threadedly engaged, the second transmission structure comprises a second driving gear and a second driven gear that mesh with each other, the second driving gear is arranged on the output shaft of the motor, and the second driven gear is sleeved on the inner cutter tube and is arranged to be circumferentially fixed and axially slidable relative to the inner cutter tube.

8. The method according to claim 7, wherein the number X of rotations of the motor corresponding to the axial movement distance L of the inner cutter tube is calculated according to the following method:

$$X = \frac{L}{P_2\left(\dfrac{B}{D} - \dfrac{A}{C}\right)}$$

where $P_2$ is a pitch of the fifth thread segment or the sixth thread segment, B is a number of teeth of the first driving gear, D is a number of teeth of the first driven gear, A is a number of teeth of the second driving gear, and C is a number of teeth of the second driven gear.

9. The method according to claim 7, wherein the transmission mechanism further comprises a transmission sleeve fixedly sleeved on the inner cutter tube, the transmission sleeve comprises outer threads, and the first driven gear is sleeved on the transmission sleeve and is threadedly engaged with the transmission sleeve.

10. The method according to claim 9, wherein an extension segment extends axially from the transmission sleeve, one end of the second driven gear is fixedly connected with a sleeve piece, the sleeve piece is sleeved on the extension segment and cooperates with the extension segment through a convex-concave structure to transmit torque, and the transmission sleeve is configured to be axially slidably relative to the sleeve piece to maintain torque transmission during a relative axial movement.

11. The method according to claim 10, wherein the biopsy surgical device also comprises a support housing, the inner cutter tube and the outer cutter tube are both mounted on the support housing, the support housing comprises a transmission window, and the first driven gear and the second driven gear partially extend out of the support housing through the transmission window.

12. The method according to claim 11, wherein the support housing comprises a positioning structure configured to axially position the first driven gear and the second driven gear.

13. The method according to claim 12, wherein the positioning structure comprises steps formed on the transmission window and an inner wall of the support housing, and the steps are configured to axially position the first driven gear and the second driven gear.

14. The method according to claim 11, wherein an inner wall of the support housing comprises a plurality of convex ribs, and an outer wall of the sleeve piece is supported by the convex ribs.

15. A non-transitory computer-readable storage medium with a computer program stored therein, wherein when the computer program is executed by a processor, steps of the method of claim 1 are implemented.

16. A control device for adjusting an opening size of a sampling window of a biopsy surgical device, the control device comprising:

an obtaining module configured to obtain input instructions, the input instructions at least comprising a set value of an opening length of the sampling window;

a distance calculation module configured to determine an axial movement distance of an inner cutter tube according to a current position of the inner cutter tube and the set value of the opening length of the sampling window;

a rotation number calculation module configured to calculate a number of rotations of a motor corresponding to the axial movement distance of the inner cutter tube according to a transmission relationship of a transmission mechanism; and a control module configured to control a motor to rotate according to the number of rotations, so that the inner cutter tube moves axially, and the sampling window reaches a target opening length.

17. A biopsy surgical device, comprising:

an inner cutter tube;

an outer cutter tube defining a sampling window on a side of a front end thereof, and the outer cutter tube is sleeved over the inner cutter tube;

a motor configured to drive the inner cutter tube to move axially through a transmission mechanism and control a front end of the inner cutter tube to stop at any position along an axial direction of the sampling window of the outer cutter tube, thereby adjusting an opening length of the sampling window; and a controller configured to execute a method for adjusting an opening size of the sampling window;

wherein the method comprises:

obtaining an input instruction which at least comprises a set value of an opening length of the sampling window;

determining an axial movement distance of the inner cutter tube according to a current position of the inner cutter tube and the set value of the opening length of the sampling window;

calculating a number of rotations of the motor corresponding to the axial movement distance of the inner cutter tube according to a transmission relationship of the transmission mechanism; and controlling the motor to rotate according to the number of rotations, causing the inner cutter tube to move axially, so that the sampling window reaches a target window opening length.

18. The biopsy surgical device according to claim 17, wherein the transmission mechanism comprises a transmission member fixedly connected to an output end of the motor, the transmission member comprises a first thread segment, the inner cutter tube comprises a second thread segment that threadedly engaged with the first thread segment, and the motor drives the transmission member to rotate, which in turn drives the inner cutter tube to move axially;

wherein the number X of rotations of the motor corresponding to the axial movement distance L of the inner cutter tube is calculated according to the following method:

$$X = \frac{L}{P}$$

where P is a pitch of the first thread segment or the second thread segment.

19. The biopsy surgical device according to claim 17, wherein the transmission mechanism comprises a first driving gear and a first driven gear that mesh with each other, the first driving gear is mounted on an output shaft of the motor, the inner cutter tube comprises a third thread segment, the first driven gear comprises a fourth thread segment, the first driven gear and the inner cutter tube are threadedly engaged, and the motor drives the first driving gear to rotate so that the first driven gear drives the inner cutter tube to move axially;

wherein the number X of rotations of the motor corresponding to the axial movement distance L of the inner cutter tube is calculated according to the following method:

$$X = \frac{L}{P_1 \dfrac{B}{D}}$$

where $P_1$ is a pitch of the third thread segment or the fourth thread segment, B is a number of teeth of the first driving gear, and D is a number of teeth of the first driven gear.

20. The biopsy surgical device according to claim 17, wherein the transmission mechanism comprises a first transmission structure and a second transmission structure, the second transmission structure is configured to drive the inner cutter tube to rotate around an axis thereof, an output portion of the first transmission structure is sleeved on the inner cutter tube and is threaded with the inner cutter tube, the output portion and the inner cutter tube rotate in a same direction, the output portion and the inner cutter tube are configured with a speed difference therebetween, and the inner cutter tube is driven to move axially by the speed difference and thread structures on the output portion and the inner cutter tube.

* * * * *